United States Patent [19]

Tonne et al.

[11] 4,427,600
[45] Jan. 24, 1984

[54] PREPARATION OF 1-ALKYL-2-CHLORO-5-NITROBENZENE-4-SULFONIC ACIDS

[75] Inventors: Peter Tonne, Neustadt; Elisabeth R. Mueller, Bobenheim-Roxheim; Helmut Goerth, Ludwigshafen, all of Fed. Rep. of Germany

[73] Assignee: BASF Aktiengesellschaft, Ludwigshafen, Fed. Rep. of Germany

[21] Appl. No.: 343,933

[22] Filed: Jan. 29, 1982

[30] Foreign Application Priority Data

Feb. 7, 1981 [DE] Fed. Rep. of Germany ....... 3104388

[51] Int. Cl.³ ............................................ C07C 143/24
[52] U.S. Cl. ............................. 260/505 E; 260/505 R; 260/505 S
[58] Field of Search ............. 260/505 R, 505 E, 505 S

[56] References Cited

U.S. PATENT DOCUMENTS 1,755,648  4/1930  Henle et al. .
1,759,554  5/1930  Henle et al. .
4,131,619  12/1978  Pews .

FOREIGN PATENT DOCUMENTS 1427106  3/1976  United Kingdom .
1440991  6/1976  United Kingdom .

OTHER PUBLICATIONS

European Search Report EP 82 10 0680.6.
Roberts et al., "Basic Principles of Org. Chem.", (1965), pp. 784–803.

Primary Examiner—Alan Siegel
Attorney, Agent, or Firm—Oblon, Fisher, Spivak, McClelland & Maier

[57] ABSTRACT

A process for the preparation of compounds of the formula I

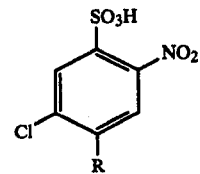

where R is alkyl, by sulfonation, chlorination and nitration starting from an alkylbenzene, wherein the alkylbenzene is sulfonated with from 2.5 to 3, preferably from 2.65 to 2.75, moles of concentrated sulfuric acid per mole of alkylbenzene, the reaction product is then reacted with from about 1.1 to 1.3 moles of chlorine in the absence of a catalyst, the product is subsequently nitrated with highly concentrated nitric acid at elevated temperatures and the nitro compound is isolated.

3 Claims, No Drawings

PREPARATION OF 1-ALKYL-2-CHLORO-5-NITROBENZENE-4-SULFONIC ACIDS

The present invention relates to a process for the preparation of compounds of the formula I

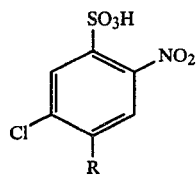

where R is alkyl, by sulfonation, chlorination and nitration starting from an alkylbenzene, wherein the alkylbenzene is sulfonated with from 2.5 to 3, preferably from 2.65 to 2.75, moles of concentrated sulfuric acid per mole of alkylbenzene, the reaction product is then reacted with from about 1.1 to 1.3 moles of chlorine in the absence of a catalyst, the product is subsequently nitrated with highly concentrated nitric acid at elevated temperatures and the nitro compound is isolated.

R is, in particular, alkyl of 1 to 4 C atoms, preferably methyl or ethyl.

The process according to the invention is advantageously carried out by adding 96–98% strength sulfuric acid to the alkylbenzene in a manner such that the temperature remains at from 100° to 130° C., preferably from 105° to 110° C. The sulfonation, which can also be carried out under superatmospheric pressure ($\leq 6$ bar), as a rule takes from 1 to 10 hours.

Chlorine is then introduced at from about 50° to 100° C., preferably from 60° to 80° C., until the alkylsulfonic acid is consumed.

About the molar amount or more, based on alkylbenzene, of highly concentrated nitric acid is then added at from about 35° to 100° C., preferably from 60° to 70° C. For the purposes of the invention, highly concentrated nitric acid is preferably about 98–100% strength acid; if the concentration is lower, the amount must be correspondingly increased.

When the nitration has ended, the nitro compound can be precipitated by adding water, and isolated, advantageously from about 50–60% strength sulfuric acid.

Details of the reaction procedure can be found in the Examples, in which, unless indicated otherwise, parts and percentages are by weight.

The nitro compounds prepared according to the invention can be reduced to the amino compounds in a conventional manner (for example by Béchamp reduction or by catalytic hydrogenation). The amino compounds are useful diazo components for the preparation of pigments, for example Lackrot-C pigments.

FIAT 1313 I, pages 123 to 126, German Laid-Open Application DOS 2,627,054 and Japanese Preliminary Published Application 79/19 935, for example, have already disclosed processes for the preparation of the compounds of the formula I.

All the conventional processes, however, give a lower overall yield, generally of about 45%.

EXAMPLE 1

93.8 parts by weight of toluene are heated at 105° C. and 281.1 parts by weight of concentrated sulfuric acid are added at from 105° to 110° C. in the course of 2 hours. After the addition of sulfuric acid, the reaction mass is stirred and is then cooled to 65°–70° C. 75 parts by weight of chlorine are introduced at this temperature in the course of 12 hours. The mixture is then cooled to 60° C. and 65.3 parts by weight of highly concentrated nitric acid are introduced at from 60° to 65° C. in the course of one hour.

442 g of a mixture are obtained, which, according to HPLC, contains 179.5 parts of 2-chloro-5-nitro-p-toluenesulfonic acid, ie. 70% of theory (based on the toluene employed).

The mixture is diluted with water until a 50% strength by weight sulfuric acid is obtained. On cooling to 20° C., the nitro compound precipitates, and is filtered off.

175 parts by weight of the nitro compound are thus obtained in a purity of 95% (HPLC).

The yield is 65.7% of theory (based on the toluene).

A further 10 parts of the nitro compounds can be obtained by working up the filtrate. HPLC=High Pressure Liquid Chromatography

EXAMPLE 2

159 parts of ethylbenzene are heated at from 105° to 108° C. and a total of 413 parts of concentrated sulfuric acid are added in the course of 2 hours, during which the temperature should not exceed 110° C.

After the addition of the sulfuric acid, the reaction mass is stirred for one hour and then cooled to 65°–70° C. 110 parts of chlorine gas are then introduced at this temperature in the course of 14 hours.

The reaction mixture is subsequently cooled to 60°–65° C. and 96.5 parts of highly concentrated nitric acid are introduced within this temperature range.

When the reaction has ended, the reaction mass is run into a mixture of 105 parts of water and 550 parts of 60% strength sulfuric acid, the mixture is cooled to 20° C. and the precipitated 1-ethyl-2-chloro-5-nitrobenzene-4-sulfonic acid is filtered off with suction. 303 parts of product are obtained, ie. 76% of theory (based on ethylbenzene).

A further 16 parts of sulfonic acid, ie. 4.1% of theory, can be obtained by working up the mother liquor.

Bechamp reduction of the combined purified Na salt solutions of 1-ethyl-2-chloro-5-nitrobenzene-4-sulfonic acid gives 261.5 parts of 5-amino-2-chloro-p-ethylbenzenesulfonic acid, ie. 74% of theory (based on ethylbenzene).

According to HPLC, the product is 98.9% pure.

We claim:

1. A process for the preparation of a 1-alkyl-2-chloro-5-nitro-benzene-4-sulfonic acid of the formula

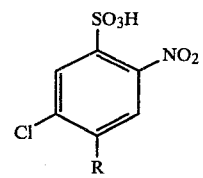

where R is alkyl, by sequential sulfonation, chlorinatiion and nitration starting from an alkylbenzene, wherein the alkylbenzene is sulfonated at temperatures between about 100° to 130° C. with from 2.5 to 3 moles of concentrated sulfuric acid per mole of alkylbenzene, the reaction product is then reacted at temperatures between about 60° to 80° C. with from about 1.1 to 1.3 moles of chlorine in the absence of a catalyst, the product is subsequently nitrated with highly concentrated nitric acid at elevated temperatures, and the resulting compound of said formula is isolated.

2. A process according to claim 1, wherein the sulfonation is performed at a temperature from 105° to 110° C.

3. A process according to claim 1, wherein the nitration is performed at a temperature from 60° to 70° C. with 98 to 100% strength acid.

* * * * *